(12) United States Patent
Mantsch et al.

(10) Patent No.: US 9,042,998 B2
(45) Date of Patent: May 26, 2015

(54) MEDICAL ELECTRODE SYSTEM

(76) Inventors: Christian Mantsch, Minden (DE); Uwe Stumpp, Frittlingen (DE)

( * ) Notice: Subject to any disclaimer, the term of this patent is extended or adjusted under 35 U.S.C. 154(b) by 1758 days.

(21) Appl. No.: 11/813,416

(22) PCT Filed: Jan. 11, 2006

(86) PCT No.: PCT/EP2006/000193
§ 371 (c)(1),
(2), (4) Date: Jul. 5, 2007

(87) PCT Pub. No.: WO2006/074917
PCT Pub. Date: Jul. 20, 2006

(65) Prior Publication Data
US 2008/0215126 A1    Sep. 4, 2008

(30) Foreign Application Priority Data

Jan. 13, 2005  (DE) .................... 20 2005 000 544 U

(51) Int. Cl.
*A61N 1/05* (2006.01)
*A61N 1/36* (2006.01)

(52) U.S. Cl.
CPC .......... *A61N 1/0551* (2013.01); *A61N 1/36071* (2013.01)

(58) Field of Classification Search
CPC .................... A61N 1/0551; A61N 1/36071
USPC ............ 607/117, 119, 122; 604/890.1, 891.1, 604/892.1
See application file for complete search history.

(56) References Cited

U.S. PATENT DOCUMENTS

| | | | | |
|---|---|---|---|---|
| 4,407,298 A | * | 10/1983 | Lentz et al. | 600/526 |
| 5,121,754 A | | 6/1992 | Mullett | |
| 5,683,255 A | * | 11/1997 | Menze | 439/63 |
| 5,713,923 A | * | 2/1998 | Ward et al. | 607/3 |
| 6,162,202 A | * | 12/2000 | Sicurelli et al. | 604/272 |
| 2002/0198568 A1 | | 12/2002 | Hafer et al. | |
| 2003/0135253 A1 | | 7/2003 | Kokones et al. | |
| 2004/0044369 A1 | * | 3/2004 | Roy | 607/4 |
| 2004/0210290 A1 | | 10/2004 | Omar-Pasha | |
| 2006/0178594 A1 | * | 8/2006 | Neubardt et al. | 600/547 |

FOREIGN PATENT DOCUMENTS

| | | |
|---|---|---|
| DE | 20308422 U1 | 11/2004 |
| EP | 1181947 A2 | 2/2002 |

* cited by examiner

*Primary Examiner* — Carl H Layno
*Assistant Examiner* — Jennifer Ghand
(74) *Attorney, Agent, or Firm* — Richard M. Goldberg

(57) ABSTRACT

An electrode system includes an implantable flexible electrode, especially an epidural electrode, having at least one distal electrical contact (12). The electrode includes a subcutaneously implantable port (26), a probe that can be introduced into the port (26) forms part of the electrode system with at least one probe contact (53), and at least one electrical contact element (56) connected to the distal contact (12) is arranged in the port (26) in order to generate an electrical connection with the probe contact (53).

14 Claims, 2 Drawing Sheets

MEDICAL ELECTRODE SYSTEM

BACKGROUND OF THE INVENTION

The invention relates to an electrode system comprising an implantable, flexible electrode, particularly an epidural electrode, comprising at least one distal electrical contact. According to a further development, the electrode is arranged in an implantable, flexible catheter, particularly an epidural catheter.

Generally, such a catheter has at least one channel which, for example, is used to administrate drugs via the catheter. Sometimes, however, an electrode without a channel is also called a catheter, for example, a stimulation catheter. Such catheters with a distal electrical contact which do not comprise a channel and therefore are not a catheter in its actual sense, are subsequently called electrodes.

Catheters are known technical medical products which are manufactured for various intended purposes of usage in diagnostics or therapy. For example, epidural catheters are known which can be inserted by a physician into the epidural space in the region of the spinal canal so as to be able to inject pain-killing drugs, for example. Such a method is particularly applied in treatment of chronic pain. The catheter can remain in the body for a time period of 1 to 30 days, for example, and the injection of the drugs can be effected through external or implanted pumps.

Instead of catheters also electrodes are used in therapy of chronic pain. For example, electrodes for implantation are known which are connected to a pulse generator for permanent stimulation of the spinal cord or the nerves.

Moreover, special needles are known which are connected to a generator of pulsed high frequency. Such special needles and high frequency generators are used to trigger the release of pain-inhibiting substances in the spinal cord by selectively stimulating nerves, thereby effecting a pain treatment. However, usage of these special needles is frequently limited due to anatomical reasons or is avoided because of the risk of injury at introducing the special needles.

From EP 1 181 947 A2, an epidural catheter is known having at least three electrodes arranged in line. The electrodes serve to electrically stimulate nerves or the spinal cord. A channel for administration of drugs can be provided, so that, in addition to the electrical stimulation of the spinal cord or the spinal nerves, an injection of pain-killing drugs is possible.

A further implantable epidural catheter is known from DE 203 08 422 U1. This catheter is, for example, suitable for applying pulsed high frequency for stimulation of nerves. Furthermore, a syringe or a drug pump can be connected. The catheter comprises a fixation member which can serve to fasten the catheter at a point of entry into a body and through which electrical leads and a hose line of the catheter are led.

SUMMARY OF THE INVENTION

It is an object of the present invention to provide an electrode system of the kind mentioned Initially, comprising a catheter or an electrode, the system offering a more flexible application of the system.

According to the invention, this object is achieved by providing an electrode system of the kind mentioned initially, wherein the electrode comprises a port which is subcutaneously implantable, wherein a probe comprising at least one probe contact is introduceable into the port and forms a part of the electrode system, and wherein at least one electrical contact element for establishing an electrical connection to the probe contact is arranged in the port, said electrical contact element being connected to the distal contact. According to a further development, the electrode is arranged in an implantable, flexible catheter, particularly an epidural catheter. In this case, an access opening of the catheter is arranged in the port.

After inserting the electrode or the catheter, the electrode/catheter can be completely implanted, including the port, beneath the skin near to the point of entry into the body. Being concealed below the skin, the catheter is less cumbersome for the patient. Moreover, the risk of infection and the risk of complications are reduced. Thus, the electrode system according to the invention allows, for example, after an ambulatory stimulation treatment of a patient to leave the electrode or the catheter inside the body of the patient and to dismiss the patient to go home until a new stimulation will be necessary after, for example, some days or weeks. Then, for example, a probe in the form of a needle can be introduced into the port in order to apply a stimulation current again. Thus, the electrode system according to the invention has distinct advantages regarding its application as compared to a conventional implantable electrode.

In an especially preferred embodiment, the electrical contact element and the probe contact are adapted to transmit radio frequency. Thus, a stimulation with high frequency pulses can take place.

The electrode system comprising the catheter is an advancement which also opens up an increased range of application as compared to a conventional implantable catheter or stimulation catheter. When, for example, the catheter is inserted as an epidural catheter into the area of the spinal canal, in addition to the stimulation of the spinal cord or the spinal nerves by, for example, a pulsed high frequency current, according to requirements an injection of a pain-killing drug via the port and the access opening of the catheter can take place. The implantable port can, for example, comprise a septum which is reachable from external with an injection needle.

Optionally, between the port and the catheter, a drug pump can be provided being also implantable. Thereby, an evenly distributed dispensing of drugs is achievable over a longer time period.

Optionally, an injection chamber for the catheter is arranged at the port. Thereby, the injection of drugs into the port is facilitated, and the injection chamber can also serve as a reservoir chamber for an implantable drug pump.

Further advantageous details of the invention are indicated in the dependent claims.

Preferably, the probe comprises a coupling member, and the port of the electrode or of the catheter comprises a coupling device for the coupling member. These, for example, constitute means for mechanically anchoring the probe at the port. This can, for example, be a mechanical mounting or locking mechanism, e.g. a snap fastener. In particular, a secure contact can be established between the probe contact and the electrical contact element by the coupling device and the coupling member. When the probe is held at the port, this also facilitates the application of pulses for stimulation of nerves, for example.

Preferably, a threaded shoulder constitutes the coupling member of the probe. Preferably, a threaded member constitutes the coupling device. For example, a probe can be screwed into the latter with the threaded shoulder.

According to a preferred embodiment of the electrode or the catheter, the port comprises a septum for being punctured it with a needle. For example, the needle constitutes the probe. Alternatively, the needle accommodates the probe, and the probe can be pushed forward out of the needle. Then, the electrical contact element is arranged within the port such that an electrical connection can be established to at least one probe contact of the probe. Furthermore, in the case of the coupling device, for example, the coupling device is also arranged in relation to the septum in such a manner that the probe can be coupled to the coupling device. A septum has the advantage that the interior space of the port is insulated and sealed against the surroundings both with and without a needle penetrating the septum.

Preferably, a guide member is provided at the port, which guide member guides the probe to the electrical contact element and, if applicable, to the coupling device.

BRIEF DESCRIPTION OF THE DRAWINGS

Preferred embodiments will be described below with reference to the drawings, wherein.

For reasons of clarity, the drawings are not drawn to scale.

DETAILED DESCRIPTION

Figure 1:
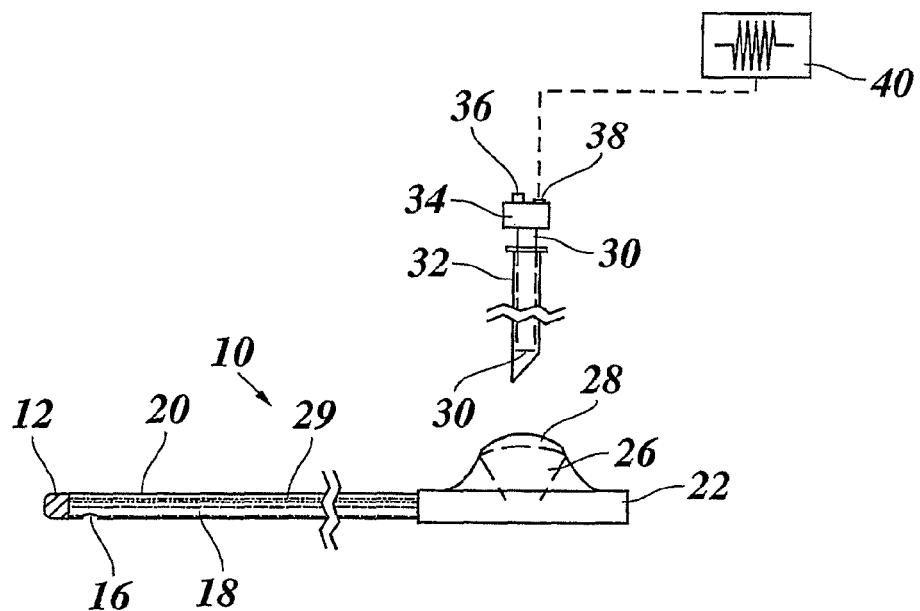
FIG. 1 is a schematic view of an epidural catheter having an implantable port and of a needle which accommodates a probe.

The epidural catheter 10 shown in FIG. 1 comprises, in its distal region, an electrical contact 12, which forms a cap encasing the end of the catheter 10. The contact 12 is drawn with hatching. A lateral aperture 16 of a hose line 18 of the catheter is arranged next to the contact 12. The edge of the electrical contact 12 is flush with a sheathing 20 of the catheter 10 made of silicone rubber. The outer diameter of the sheathing 20 is 1.33 mm, corresponding to a specification of 4 French. In the longitudinal direction of the catheter 10, the contact 12 extends to a length approximately corresponding to the outer diameter of the sheathing 20.

At the proximal end of the catheter 10, the catheter is seamlessly connected to a flat casing 22. The upper wall of the casing 22 comprises a bulge in which a port 26 is formed, the upper wall of the port 26 being formed by a pricking septum 28. Via the pricking septum 28, the port 26 is accessible from external by an injection needle, for example. The pricking septum 28 is made in a known manner such that its wall is sufficiently dense and elastic so as to provide a reliable sealing again, after an injection needle previously inserted through the septum has been retracted.

Inside the catheter 10, an electrical lead 29 for the electrical contact 12 runs inside the sheathing 20 parallel to the hose line 18 and is, like the hose line 18, indicated with dashed lines. The configuration of the catheter 10 will be further explained below with reference to FIG. 2.

In a known manner, an aseptic guide wire (not shown) is arranged inside the hose line, which guide wire serves to shift the catheter 10 to the desired position in the spinal canal and is then retracted. An introduction aperture for the guide wire is sealed before the casing 22 is implanted. The guide wire is slightly bendable in the region of its leading end.

The probe 30 shown in FIG. 1 is accommodated within a needle 32 and is slideably guided therein. At its rear end, it is connected to an adapter 34 on which a connector 36 for a syringe or a drug pump and an electrical connector 38 are arranged. The electrical connector 38 is adapted to be directly or via an adapter (now shown) connected to a pulse generator 40, which generates a pulsed high frequency current. The pulse generator 40 can, for example, be the device N50 of the company Stryker How Medica, the device RFG-3C+ of the company Radionics or the device Neurotherm of the company RDG Medical.

Figure 2:
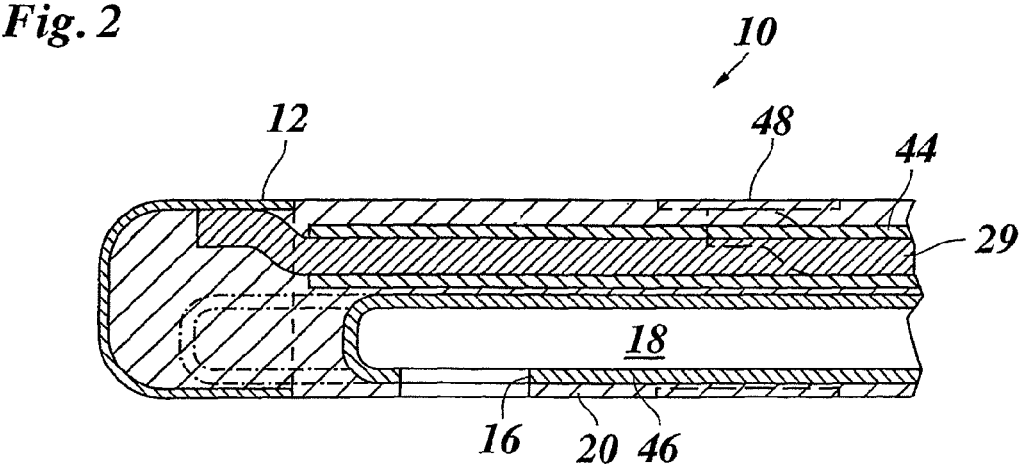
FIG. 2 is a schematic longitudinal sectional view of the tip of the epidural catheter.

FIG. 2 shows the tip of the catheter 10 as a longitudinal sectional view. The electrical lead 29 runs parallel to the hose line 18, said lead 29 being internally soldered to the electrical contact 12. The electrical lead 29 comprises an insulation 44 and runs within a thickened region of the wall of the sheathing 20. The hose line 18 is formed by an additional internal tubular layer 46 inside the sheathing 20. The sheathing 20 encloses the tube formed by the internal layer 46 as well as the insulation 44. The internal layer 46 is isolated from the contact 12 by the sheathing 20. At least at the aperture 16, which penetrates the layer 46 and the sheathing 20, the internal layer 46 is tightly connected to the sheathing 20. However, the internal layer 46 can also be a part of a sheathing of the catheter constituted of two or more layers.

The tube formed by the inner layer 46 ends on the other side of the aperture 16. It can, however, also extend into the cap formed by the distal contact 12, as indicated by chain dotted lines.

Alternatively to or additionally to the cap-shaped electrical contact 12, however, there can also be provided an annular contact 48 near the lateral aperture 16, as is indicated by dashed lines. Then, an aperture at the end of the catheter 10 can be provided alternatively to the lateral aperture 16.

Figure 3:
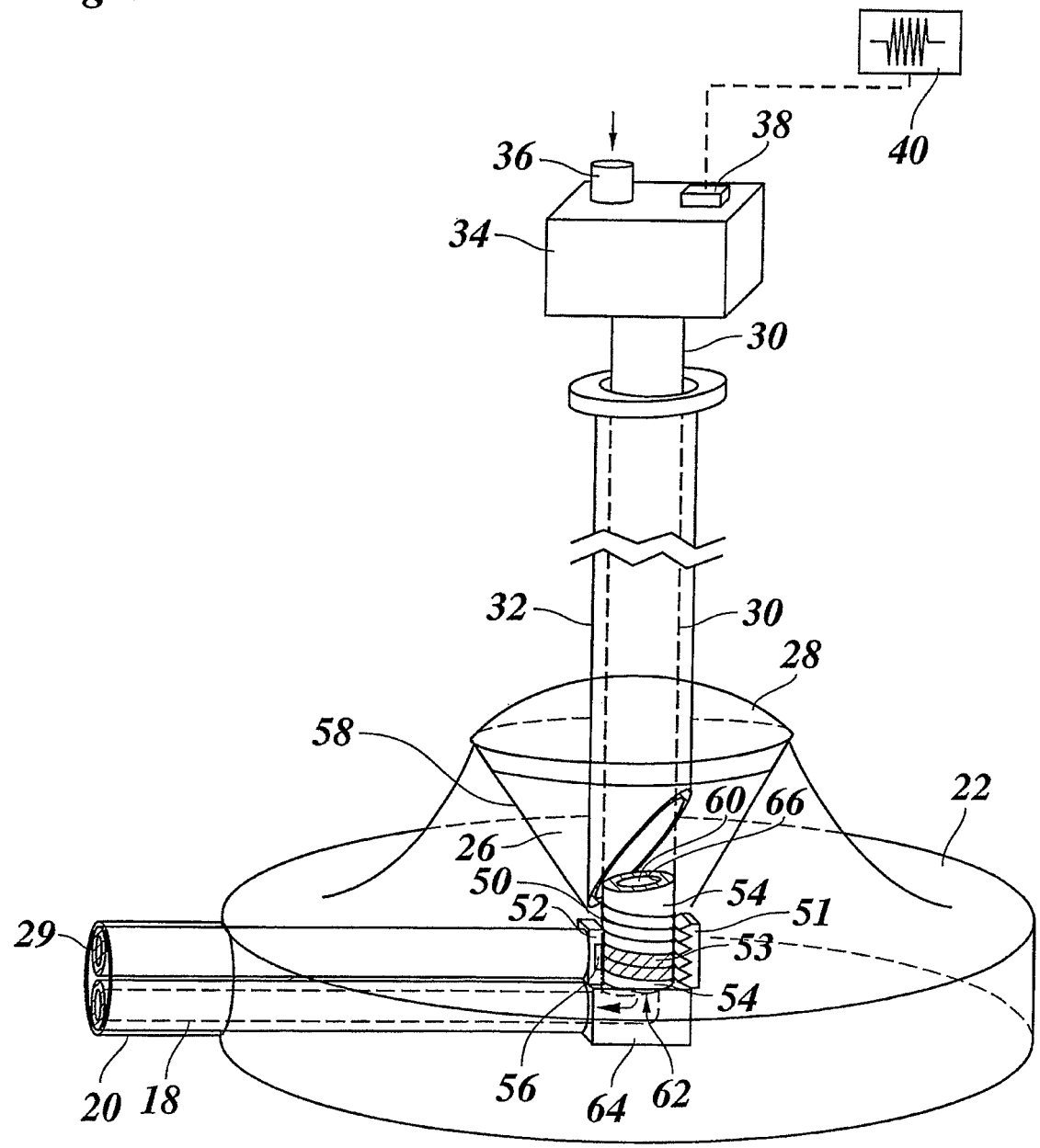
FIG. 3 is a schematic, perspective view of the port, into which the probe has been introduced.

In FIG. 3, the pricking septum 28 has been punctured by the needle 32, and the probe 30 has been introduced into the port 26 through the needle 32. The lower region of the probe 30 is shown in section.

At its lower end, the probe 30 comprises a threaded shoulder 50 which is screwed into a socket being formed inside the casing 22 and having a threaded member 51 and a counterpiece 52.

In the region of the threaded shoulder 50, the probe 30 comprises an electrically conducting region which forms a probe contact 53 drawn with hatching and which, for example, extends over the height of two thread turns. Above and below the probe contact, the outer wall of the probe comprises an insulating sheathing 54.

The threaded shoulder 50 with the probe contact 53 is retained between the threaded member 51 and the counterpiece 52, the latter comprising an electrical contact element 56. The electrical contact element 56 extends over a limited height region of the counterpiece 52 and lies approximately at a height at which the probe contact 53 is situated when the probe 30 is screwed into the socket against a stop. In this manner, an electrical connection between the probe contact 53 and the electrical contact element 56 being connected to the electrical lead 29 is established. At the same time, the probe 30 is mechanically coupled to the casing 22 of the port 26. Here, the threaded shoulder 50 constitutes a coupling member of the probe 30, and the socket with the threaded member 51 and the counterpiece 52 constitutes a coupling device of the port 26.

Below the pricking septum 28, there is arranged a cone 58 at the port 26, which cone forms a guide member for the probe 30 and thus facilitates the placing of the threaded shoulder 50 in the port 26. Then, by rotating the probe 30 in the needle 32, the threaded shoulder 50 is screwed into the socket with the threaded member 51.

The probe contact 53 is connected to the electrical connector 38 of the adapter 34. Thereby, an electrical connection is established between the pulse generator 40 and the electrical contact 12 of the catheter 10. The contact 12, the lead 29, the electrical contact element 56, the probe contact 53, and the probe 30 with the adapter 34 are adapted both for applying pulses for a test stimulation of nerves or the spinal cord having, for example, a voltage in the range of 0-12 V, a frequency in the range of 50 to 150 Hz, and a pulse width in the range of 150 to 400 microseconds, as well as for applying pulsed high frequency having, for example, a voltage in the range of 20 to 30 V and a pulsed frequency of, for example, 50 kHz or 500 kHz and a pulse width of 20 milliseconds. The numerical values given are only examples to illustrate the range of application of the catheter.

Thus, using high frequency pulses with an epidural catheter, for example, by stimulating the nerves inside the spinal canal, in many cases a treatment or stimulation of nerve tissue with special needles in front of the spinal column or in dangerous regions can be avoided and also those nerves can be treated with high frequency pulses which otherwise would not have been accessible for this treatment.

An access duct 60 runs inside the probe 30, said duct 60 being open at its bottom end and being connected to the connector 36 of the adapter 34 at its upper end. The bottom end of the access duct 60 is arranged in front of an access opening 62 of a connecting member 64 of the port 26, when the threaded shoulder 50 is screwed to the threaded member 51. Via the connecting member 64, the access opening 62 is connected to the hose line 18 of the catheter 10 and thus to the aperture 16.

The wall of the access duct 60 comprises an insulation layer 66 which is connected to the insulation sheathing 54 at the bottom end of the probe 30, so that the access duct 60 is electrically isolated from the probe contact 53 and its lead to the electrical connector 38. In the example shown, the probe 30 is that far screwed into the socket with the screwed member 51 that the probe 30 is tightly attached to the connecting member 64. Thereby, the probe contact 53 and the electrical contact element 56 are sealed against the access duct 60 and the access opening 62 of the catheter 10, so that a liquid being situated in the access duct 60 and the hose line 18 does not get in contact with the probe contact 53. Optionally, the sealing can be effected, for example, also at the outer circumference of the threaded shoulder 50 below the electrical contact element 56.

After the implanting of the catheter 10, the probe 30 and the catheter 10 allow, at a later, further treatment of the patient, to get along with introducing the needle 32 with the probe 30 into the port 26 without requiring further surgery. Moreover, due to the proximity of the contact 12 to the distal aperture 16 of the catheter 10, the advantage results that during insertion of the catheter 10, the location of the catheter can be checked with a test stimulation with reduced voltage and frequency. Another advantage is that the x-ray contrast of the contact is sufficiently high to allow a positioning of the catheter with x-ray monitoring without application of a contrast agent. A further advantage is that the same area can be treated with drugs as well as with electrical stimulation without having to alter the location of the catheter. Thus, for example, a drug can be injected into the catheter 10 via the connector 36.

Optionally, a sealing of the connection between the access duct 60 and the hose line 18 by the connecting member 64 or by the socket with the threaded member 51 can be dispensed with, for example, because the inside of the port 26 is in any case always sealed against the body of the patient by the pricking septum 28, and because a contact of the liquid to the electrical contact element 56 can be acceptable as the case may be.

By leaving out the hose line 18, the lateral aperture 16 and the connecting member 64 from the described catheter 10, an embodiment of an epidural electrode according to the invention is obtained. An embodiment of the probe adapted thereto results, for example, by leaving out the access duct 60 and the connector 36 at the adapter 34.

The described embodiments of the electrode, the catheter and the probes are to illustrate a possible arrangement and contacting of the probe contact 53 and the electrical contact element 56 as well as a possible connection between an access duct 60 and the hose line 18 and shall present one possibility of the realization of the port.

It is understood that the electrode system according to the Invention can also have a configuration which differs hereof. For example, at least one further electrical contact can be provided next to the electrical contact 12, and the electrical contacts can be connected to separate probe contacts via separate contact elements, said probe contacts being, for example, arranged at different heights. Then, the counterpiece 52 can be extended correspondingly. Further electrical connections can be provided, for example, for a temperature sensor arranged in the distal region of the catheter, the connection leads of which being arranged within the catheter.

Also, the realization of the coupling member of the probe 30 and of the coupling device of the catheter 10 as a threaded shoulder 50 and a threaded member 51 with counterpiece 52 is merely one possible embodiment. Thus, for example, a click-in-fastener or other mechanical anchoring is also possible.

The invention claimed is:

1. Electrode system comprising:
an implantable, flexible electrode, said electrode including:
at least one distal electrical contact,
a completely subcutaneously implantable casing having a completely subcutaneously implantable port, said port including a coupling device arranged inside of the casing, and
at least one electrical contact element arranged within said casing in said port, said at least one electrical contact element being connected to the at least one distal contact,
such that the casing seals an inside of the port and said at least one electrical contact element relative to a body patient when said port, said casing and said at least one electrical contact element are subcutaneously implanted in the body of the patient; and
a probe separate from said electrode and which is introduceable into the port from outside of the body of the patient, said probe comprising:
at least one probe contact for establishing an electrical connection with the at least one electrical contact element,
a coupling member adapted to be received by the coupling device so as to establish an electrical contact between the probe contact and the at least one electrical contact element of the electrode, and
wherein a needle accommodates the probe, and the probe is adapted to be pushed forward out of the needle.

2. Electrode system according to claim 1, wherein the electrical contact element and the at least one probe contact are adapted to transmit radio frequency signals.

3. Electrode system according to claim 1, wherein the coupling device of the port comprises a threaded member, and the coupling member of the probe comprises a threaded shoulder.

4. Electrode system according to claim 1, wherein a part of a wall of the port is formed by a septum adapted to be punctured by a needle, and an inside of the port and the casing, including the at least one electrical contact element arranged in the port, is sealed by the septum.

5. Electrode system according to claim 1, further comprising an implantable, flexible catheter having a hose line, and wherein the electrode is arranged in the implantable, flexible catheter, and the catheter includes an access opening arranged in the port, with the access opening being in fluid communication with the hose line.

6. Electrode system according to claim 5, wherein the probe comprises an access duct for communicating with the access opening of the catheter.

7. Electrode system according to claim 6, wherein the at least one probe contact is electrically insulated against an inside of the access duct.

8. Electrode system according to claim 6, wherein the port comprises a connecting member that comprises the access opening and the probe and the port are configured such that the at least one probe contact and the electrical contact element are sealable against the access duct and the access opening of the catheter by attaching the probe to the connecting member of the port.

9. Electrode system according to claim 1, wherein the implantable, flexible electrode is an epidural electrode.

10. Electrode system according to claim 5, wherein the implantable, flexible catheter is an epidural catheter.

11. Electrode system according to claim 1, wherein the coupling member and the coupling device are adapted to mechanically anchor the probe at the port.

12. Implantable, flexible catheter comprising:
a hose line,
at least one distal electrical contact,
a completely subcutaneously implantable casing having a completely subcutaneously implantable port, said port including a coupling device arranged inside of the casing,
an access opening arranged in the port and being in fluid communication with the hose line, and
at least one electrical contact element arranged within said casing in said port, said at least one electrical contact element being connected to the at least one distal contact,
such that the casing seals an inside of the port and said at least one electrical contact element relative to a body of a patient when said port, said casing and said at least one electrical contact element are subcutaneously implanted in the body of the patient; and
wherein the coupling device is adapted to receive a coupling member of a probe, which is introduceable into the port and which has at least one probe contact and an access duct for communicating with the access opening of the catheter, so as to establish an electrical contact between the at least one probe contact and the at least one electrical contact element of the catheter.

13. Electrode system comprising:
an implantable, flexible electrode, said electrode including:
at least one distal electrical contact,
a completely subcutaneously implantable casing having a completely subcutaneously implantable port, said port including a coupling device arranged inside of the casing, and
at least one electrical contact element arranged within said casing in said port, said at least one electrical contact element being connected to the at least one distal contact,
such that the casing seals an inside of the port and said at least one electrical contact element relative to a body of a patient when said port, said casing and said at least one electrical contact element are subcutaneously implanted in the body of the patient;
a probe separate from said electrode and which is introduceable into the port from outside of the body of the patient, said probe comprising:
at least one probe contact for establishing an electrical connection with the at least one electrical contact element,
a coupling member adapted to be received by the coupling device so as to establish an electrical contact between the probe contact and the at least one electrical contact element of the electrode, and
wherein a needle accommodates the probe, and the probe is adapted to be pushed forward out of the needle;
wherein a part of a wall of the port is formed by a septum adapted to be punctured by a needle, and an inside of the port and the casing, including the at least one electrical contact element arranged in the port, is sealed by the septum; and
further comprising an implantable, flexible catheter having a hose line, and wherein the electrode is arranged in the implantable, flexible catheter, and the catheter includes an access opening arranged in the port, with the access opening being in fluid communication with the hose line.

14. System comprising:
an implantable, flexible catheter, said catheter comprising:
a hose line,
at least one distal electrical contact,
a completely subcutaneously implantable casing having a completely subcutaneously implantable port, said port including a coupling device arranged inside of the casing,
an access opening arranged in the port and being in fluid communication with the hose line, and
at least one electrical contact element arranged within said casing in said port, said at least one electrical contact element being connected to the at least one distal contact,
such that the casing seals an inside of the port and said at least one electrical contact element relative to a body of a patient when said port, said casing and said at least one electrical contact element are subcutaneously implanted in the body of the patient, and
a probe separate from said catheter and which is introduceable into the port from outside of the body of the patient, said probe comprising:
an access duct for communicating with the access opening of the catheter,
at least one probe contact for establishing an electrical connection with the at least one electrical contact element,
a coupling member adapted to be received by the coupling device so as to establish an electrical contact between the probe contact and the at least one electrical contact element of the catheter, and
wherein a needle accommodates the probe, and the probe is adapted to be pushed forward out of the needle;
wherein a part of a wall of the port is formed by a septum adapted to be punctured by a needle, and an inside of the port of the casing, including the at least one electrical contact element arranged in the port, is sealed by the septum.

* * * * *